US012718373B2

(12) United States Patent
Takahashi et al.

(10) Patent No.: US 12,718,373 B2
(45) Date of Patent: Aug. 25, 2026

(54) STORAGE MEDIUM, INFORMATION PROCESSING APPARATUS, INFORMATION PROCESSING METHOD, AND INFORMATION PROCESSING SYSTEM

(71) Applicant: Konica Minolta, Inc., Tokyo (JP)

(72) Inventors: Hidekazu Takahashi, Toyonaka (JP); Hisashi Wada, Tokyo (JP); Kei Okabayashi, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 466 days.

(21) Appl. No.: 18/185,046

(22) Filed: Mar. 16, 2023

(65) Prior Publication Data

US 2023/0316526 A1 Oct. 5, 2023

(30) Foreign Application Priority Data

Mar. 29, 2022 (JP) ................................ 2022-052704

(51) Int. Cl.
*G06T 7/00* (2017.01)
*G16H 30/20* (2018.01)

(52) U.S. Cl.
CPC .......... *G06T 7/0016* (2013.01); *G16H 30/20* (2018.01); *G06T 2207/30096* (2013.01)

(58) Field of Classification Search
CPC ......... G06T 7/0016; G06T 2207/30096; G06T 2207/10068; G06T 2207/10081; G06T 2207/10088; G06T 11/20–60; G16H 30/20; G16H 50/20; G16H 30/40
See application file for complete search history.

(56) References Cited

U.S. PATENT DOCUMENTS

| | | | | |
|---|---|---|---|---|
| 2017/0301092 A1* | 10/2017 | Kikuchi | ................ | G06T 7/0016 |
| 2018/0053300 A1* | 2/2018 | Podilchuk | ............ | G06T 7/0016 |
| 2020/0327979 A1* | 10/2020 | Ishii | ...................... | G06T 7/0014 |
| 2021/0056690 A1* | 2/2021 | Futamura | ............. | G06T 7/0012 |
| 2023/0151403 A1* | 5/2023 | Slotsbo | .................. | C12M 41/36 435/32 |

(Continued)

FOREIGN PATENT DOCUMENTS

| | | |
|---|---|---|
| JP | H04-129538 A | 4/1992 |
| JP | 2008-259622 A | 10/2008 |

(Continued)

OTHER PUBLICATIONS

Office Action, dated Aug. 19, 2025, which was issued for the corresponding Japanese Patent Application No. 2022-052704, 21 pages, with English translation.

(Continued)

*Primary Examiner* — Atiba O Fitzpatrick
(74) *Attorney, Agent, or Firm* — LUCAS & MERCANTI, LLP

(57) ABSTRACT

A non-transitory computer-readable storage medium stores a program to cause a computer to perform: acquiring a first analysis result obtained by a computer process on a first medical image of a patient; acquiring a second analysis result obtained by a computer process on a second medical image of the patient; and comparing the first analysis result and the second analysis result and in a situation in which there is a difference, outputting in a manner different from the situation in which there is no difference.

16 Claims, 11 Drawing Sheets

(56) References Cited

U.S. PATENT DOCUMENTS

| | | | | |
|---|---|---|---|---|
| 2023/0197253 | A1* | 6/2023 | Nakamura | A61B 6/00 382/128 |
| 2023/0252636 | A1* | 8/2023 | Neumann | G06T 7/13 382/132 |
| 2023/0351586 | A1* | 11/2023 | Brynolfsson | G06T 7/11 |
| 2024/0046472 | A1* | 2/2024 | Highnam | G06T 7/0012 |

FOREIGN PATENT DOCUMENTS

| | | | |
|---|---|---|---|
| JP | 4651353 | B2 | 3/2011 |
| JP | 2020-173614 | A | 10/2020 |

OTHER PUBLICATIONS

Office Action, dated Nov. 4, 2025, which was issued for the corresponding Japanese Patent Application No. 2022-052704, 26 pages, with English translation.

Office Action, dated Mar. 31, 2026, which was issued for the corresponding Japanese Patent Application No. 2022-052704, 11 pages, with English translation.

* cited by examiner

| IMAGE ID | PATIENT ID | IMAGED DATE/ TIME | MODALITY | SITE | DIRECTION | ··· | ANALYSIS RESULT ID |
|---|---|---|---|---|---|---|---|
| | | | | | | | |
| | | | | | | | |
| | | | | | | | |
| | | | | | | | |
| | | | | | | | |

FIG.4

STORAGE MEDIUM, INFORMATION PROCESSING APPARATUS, INFORMATION PROCESSING METHOD, AND INFORMATION PROCESSING SYSTEM

REFERENCE TO RELATED APPLICATIONS

The entire disclosure of Japanese Patent Application No. 2022-052704, filed on Mar. 29, 2022, including description, claims, drawings and abstract is incorporated herein by reference in its entirety.

TECHNICAL FIELD

The present invention relates to a storage medium, an information processing apparatus, an information processing method, and an information processing system.

DESCRIPTION OF THE RELATED ART

Lately, a Computer Aided Detection/Diagnosis (CAD) system has been put into use. According to such system, a medical image is analyzed using a computer, a lesion candidate detected by the image analysis is presented to a physician, and the physician is requested to make a judgement.

For example, there is a proposed technique used in a CAD system that performs analysis on a medical image with a CAD program. According to the technique, after acknowledging that there is additional information showing that the diagnosis by the physician is finished (for example, a signature of the physician, an annotation created by the physician, etc.), an analysis result of the medical image is displayed (see JP 4651353). According to the technique described in JP 4651353, since the analysis result by the CAD program is displayed after the physician finishes the diagnosis, it is possible to perform a fair diagnosis (interpretation of the medical image) without the physician being influenced by the result of the CAD.

SUMMARY OF THE INVENTION

However, in conventional techniques as described in JP 4651353, in the situation in which there are many lesion candidates detected by the CAD in the medical image, there are cases in which the physician overlooks lesion candidates that should be observed.

Moreover, when the lesion candidate detected by the CAD is presented, it is possible to narrow the lesion candidates that are to be displayed according to confidence or importance of the lesion candidate. However, depending on the set conditions, the number of presented lesion candidates increases.

As described above, it is a heavy burden to a person who interprets the medical image to check all of the lesion candidates included in the analysis result by the computer, and there is a possibility that the lesion is overlooked. Therefore, the person who interprets the medical image needs to interpret the medical image while efficiently recognizing from the CAD analysis result the analysis result that the person who interprets the medical image should pay attention to.

The present invention is conceived in view of the above problems of the conventional techniques, and the purpose is to prevent overlooking an analysis result obtained by computer processing on the medical image.

To achieve at least one of the abovementioned objects, according to an aspect of the present invention, a storage medium reflecting one aspect of the present invention includes a program causing a computer to perform: acquiring a first analysis result obtained by a computer process on a first medical image of a patient; acquiring a second analysis result obtained by a computer process on a second medical image of the patient; and comparing the first analysis result and the second analysis result and in a situation in which there is a difference, outputting in a manner different from the situation in which there is no difference.

According to another aspect, an information processing apparatus includes a hardware processor configured to execute, acquiring a first analysis result obtained by a computer process on a first medical image of a patient; acquiring a second analysis result obtained by a computer process on a second medical image of the patient; and comparing the first analysis result and the second analysis result and in a situation in which there is the difference, outputting in a manner different from the situation in which there is no difference.

According to another aspect an information processing method includes: acquiring a first analysis result obtained by a computer process on a first medical image of a patient; acquiring a second analysis result obtained by a computer process on a second medical image of the patient; and comparing the first analysis result and the second analysis result and in a situation in which there is the difference, outputting in a manner different from the situation in which there is no difference.

According to another aspect an information processing system including a hardware processor configured to execute, performing a computer process on a first medical image of a patient and generating a first analysis result; performing a computer process on a second medical image of a patient and generating a second analysis result; acquiring the first analysis result; acquiring the second analysis result; and comparing the first analysis result and the second analysis result and in a situation in which there is the difference, outputting in a manner different from the situation in which there is no difference.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 3 is a diagram showing a data configuration of a data management table;

FIG. 4 is a block diagram showing a functional configuration of an information processing apparatus;

DETAILED DESCRIPTION

Hereinafter, one or more embodiments of the present invention will be described with reference to the drawings. However, the scope of the invention is not limited to the disclosed embodiments.

A storage medium including a program, an information processing apparatus, an information processing method, and an information processing system according to an embodiment of the present invention is described below. However, the scope of the present invention is not limited to the embodiments or illustrated examples.

[Configuration of Medical Image Display System]

Figure 1:
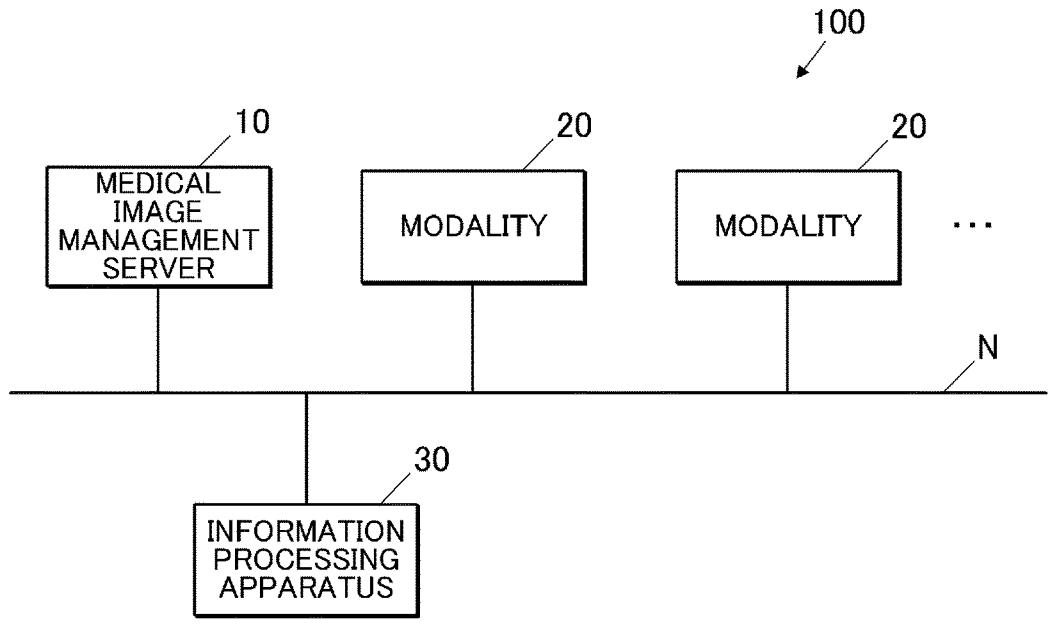
FIG. 1 is a diagram showing a system configuration of a medical image display system.

FIG. 1 shows a system configuration of a medical image display system 100 as an information processing system.

As shown in FIG. 1, the medical image display system 100 includes a medical image management server 10, modalities 20, 20, and so on, and an information processing apparatus 30. Each apparatus is able to perform data communication through a communication network N. The information processing apparatus 30 is configured to be able to connect to the medical image management server 10 as necessary through the communication network N. In the medical image display system 100, the medical image and the analysis result stored in the medical image management server 10 can be displayed on the information processing apparatus 30. These apparatuses of the medical image display system 100 are in conformity with HL7 (Health Level Seven) or DICOM (Digital Image and Communications in Medicine) standard and communicate with one another in conformity with HL7 or DICOM. The number of information processing apparatuses 30 is not limited.

The modality 20 performs imaging of a patient (subject) and generates image data of the medical image. Examples used as the modality 20 include, Computed Radiography (CR), Digital Radiography (DR), Computed Tomography (CT), Magnetic Resonance Imaging (MRI), Ultra-Sonography (US), Nuclear Medicine (NM), Endoscope (ES), and the like.

The modality 20 adds supplementary information regarding the medical image to the medical image. The supplementary information includes, patient ID, patient name, date of birth, sex, imaged date/time, image ID, modality, site, direction, etc.

The image data of the medical image generated by the modality 20 is transmitted to the medical image management server 10.

The medical image management server 10 saves and manages the image data of the medical image generated in the modality 20. For example, the medical image management server 10 may be, PACS (Picture Archiving and Communication System), etc.

The information processing apparatus 30 is a computer apparatus such as a personal computer (PC), tablet, etc. The information processing apparatus 30 is used when the user such as the physician interprets the medical image.

[Configuration of Medical Image Management Server]

Figure 2:
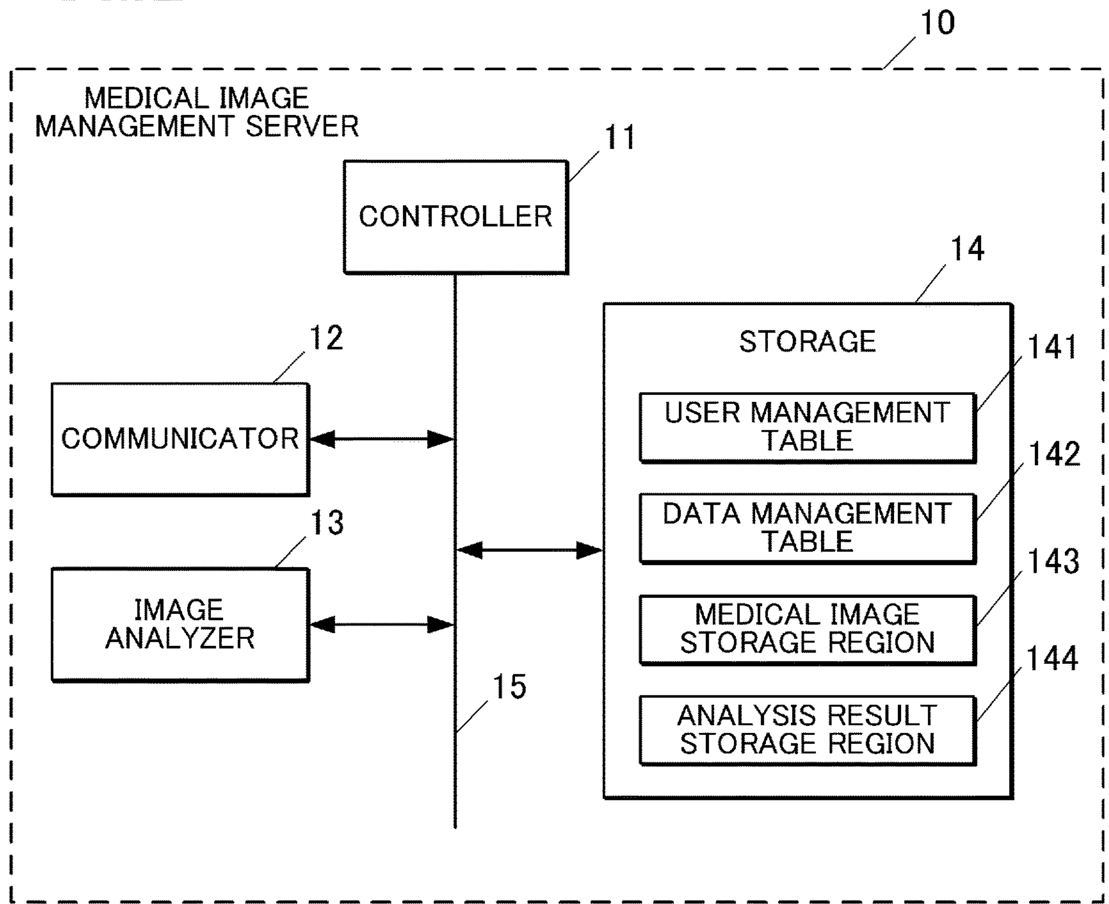
FIG. 2 is a block diagram showing a functional configuration of a medical image management server.

FIG. 2 shows a functional configuration of a medical image management server 10. The medical image management server 10 includes a controller 11, a communicator 12, an image analyzer 13, a storage 14, and the like, and the above units are connected to each other through a bus 15.

The controller 11 includes a Central Processing Unit (CPU), a Random Access Memory (RAM), and the like, and the processing operation of each unit of the medical image management server 10 is centrally controlled. Specifically, the CPU reads out various processing programs stored in the storage 14 and deploys the programs in the RAM. The various processing is performed in coordination with the program.

The communicator 12 is constituted by a network interface or the like, and transmits and receives data to/from external devices connected through the communication network N. For example, the communicator 12 receives the medical image obtained by imaging the patient with the modality 20. The communicator 12 transmits to the information processing apparatus 30 the medical image and the analysis result requested from the information processing apparatus 30.

The image analyzer 13 performs computer processing on the medical image obtained by imaging the patient and generates data of the analysis result. The computer processing is computer CAD (computer aided detection/diagnosis) processing. The image analyzer 13 detects a lesion candidate (abnormal shade candidate) from the medical image, adds annotation, and calculates an index to quantitatively evaluate the medical image. Examples of the data of the analysis result includes, Grayscale Softcopy Presentation State (GSPS) data of DICOM, overlay data, etc. The image analyzer 13 is executed by a software process performed by the CPU of the controller 11 in coordination with a program stored in the storage 14.

The storage 14 includes a Hard Disk Drive (HDD) and a non-volatile semiconductor memory, and stores various processing programs, parameters and files necessary to execute the programs, and the like.

A user management table 141 and a data management table 142 are stored in the storage 14. The storage 14 includes a medical image storage region 143 and an analysis result storage region 144.

The user management table 141 is a table to manage users (medical professionals such as physicians) who use the medical image display system 100. User ID, password, name, affiliation, e-mail address, phone number, and the like are stored in the user management table 141 corresponded to each user.

The user ID is identification information of the user.

The password is used for authentication when the user accesses to the medical image management server from the information processing apparatus 30.

The name is the name of the user.

The affiliation is information of a medical facility, medical department, etc. that the user belongs to.

The e-mail address is the e-mail address of the user.

The phone number is the phone number of the user.

The data management table 142 is a table to manage data in the medical image management server 10.

Figures 3, 4:
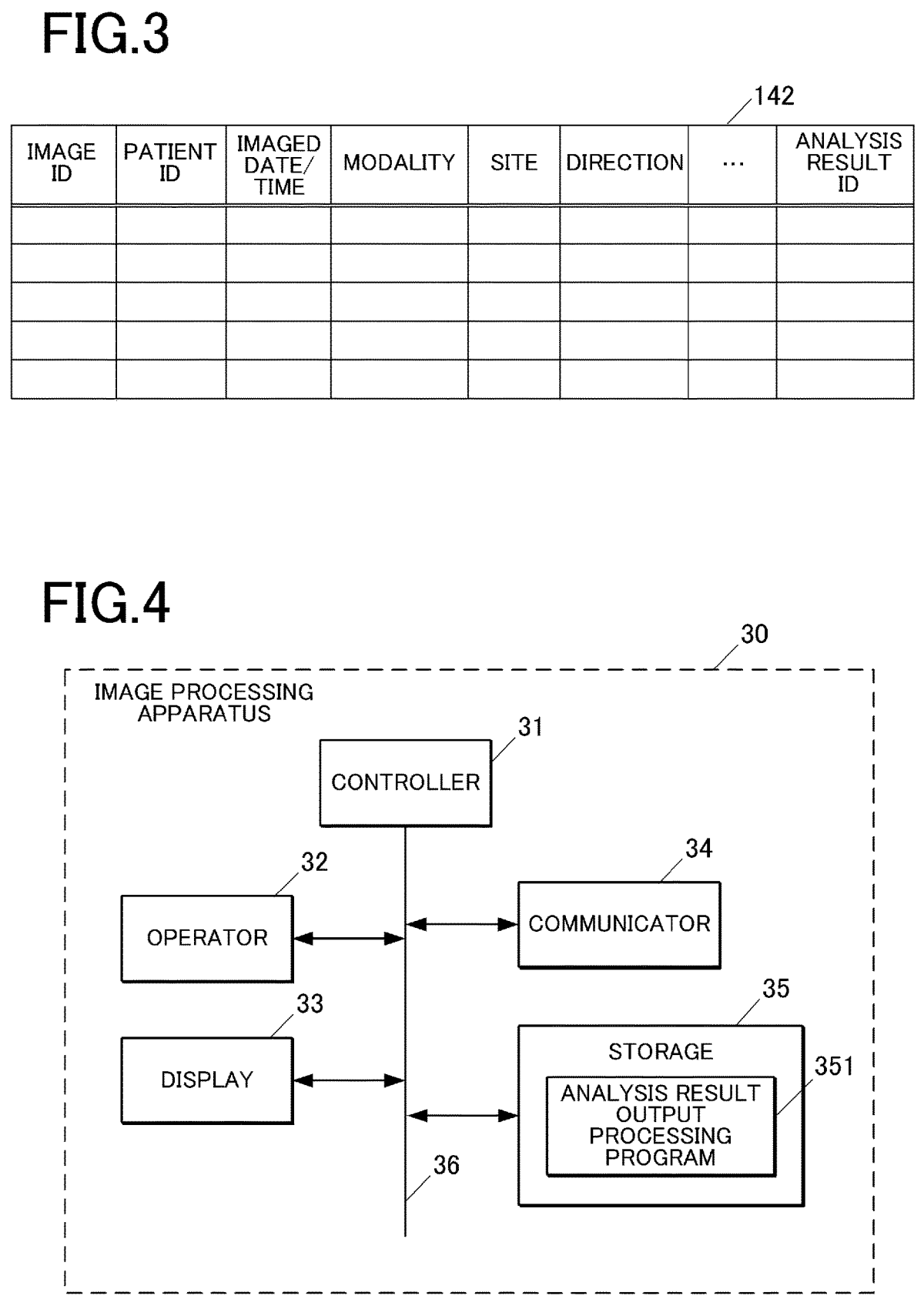

FIG. 3 is a diagram showing a data configuration of a data management table 142. Image ID, patient ID, imaged date/time, modality, site, direction, analysis result ID, etc. are stored in the data management table 142 corresponded to each medical image stored in the medical image storage region 143.

The image ID is identification information of the medical image.

The patient ID is the identification information of the patient who is the imaged target in the medical image.

The imaged date/time is the date and time when the medical image is imaged.

The modality is the modality with which the medical image is imaged.

The site is the site that is the imaged target in the medical image.

The direction is the direction that the target is imaged in the medical image.

The analysis result ID is the identification information of the analysis result obtained as a result of the image analyzer 13 analyzing the medical image.

The image data of the medical image received from the modality 20 is stored in the medical image storage region 143.

Data of the result of analysis of the medical image is stored in the analysis result storage region 144. The data of the analysis result includes, position/size/type of the lesion candidate detected from the medical image, contents/position of the annotation attached to the medical image, position of measured line drawn on the medical image, numeric value calculated from the medical image, and the like.

When the controller 11 receives the medical image from the modality 20 through the communicator 12, the medical image is stored in the storage 14 and the medical image is analyzed by the image analyzer 13.

In a situation that an acquiring request to acquire the medical image is made from the information processing apparatus 30 through the communicator 12, the controller 11 reads the medical image from the storage 14, and provides the read medical image to the information processing apparatus 30 through the communicator 12.

In the situation that the acquiring request to acquire the analysis result is made from the information processing apparatus 30 through the communicator 12, the controller 11 reads the analysis result from the storage 14, and provides the read analysis result to the information processing apparatus 30 through the communicator 12.

[Configuration of Information Processing Apparatus]

FIG. 4 shows a functional configuration of the information processing apparatus 30. The information processing apparatus 30 includes a controller 31, an operator 32, a display 33, a communicator 34, a storage 35, and the like which are not shown, and the above units are connected to each other through a bus 36.

The controller 31 includes a CPU, a RAM, and the like, and the processing operation of each unit of the information processing apparatus 30 is centrally controlled. Specifically, the CPU reads out various processing programs stored in the storage 35 and deploys the programs in the RAM. The various processing is performed in coordination with the program.

The operator 32 includes a keyboard including cursor keys, letter/number input keys and various function keys, and a pointing device such as a mouse, and outputs to the controller 31 operation signals input by key operation on the keyboard or by mouse operation. In the situation in which the operator 32 is a touch panel layered on the display 33, the operation signal according to the position touched by the user's finger is output to the controller 31.

The display 33 includes a monitor such as an LCD (Liquid Crystal Display), and displays various screens according to instructions of display signals input from the controller 31.

The communicator 34 is constituted by a network interface or the like, and transmits and receives data to/from external devices connected through the communication network N.

The storage 35 includes a HDD, a non-volatile semiconductor memory and stores various processing programs, parameters and files necessary to execute the programs, and the like. For example, an analysis result output process program 351 is stored in the storage 35. The analysis result output process program 351 is a program to perform a process to display the medical image that is the target of interpretation and the analysis result when the medical image is interpreted on the information processing apparatus 30.

The controller 31 acquires the first analysis result obtained by the computer process on the first medical image of the patient. That is, the first controller 31 functions as a first acquirer.

The controller 31 acquires the second analysis result obtained by the computer process on the second medical image imaging the same patient as the first medical image. That is, the first controller 31 functions as a second acquirer.

The first medical image is an image imaged at a different date and time from the second medical image. According to the present embodiment, the first medical image is a present image and the second medical image is a past image. The present image is the newly imaged medical image that is the target of interpretation. The past image is the medical image imaging the patient the same as the present image as the target of imaging in the past (most recent image in the situation in which there are a plurality of medical images with the imaged date/time before the present image). The past image is the medical image which is to be the target of comparison in the comparison of the analysis results.

The controller 31 compares the first analysis result with the second analysis result. In the situation in which there is a difference in the first analysis result and the second analysis result, the output is made in a manner different from the output of the situation in which there is no difference. That is, the controller 31 functions as an outputter.

The difference between the first analysis result and the second analysis result includes, the situation in which the lesion candidate detected in the first medical image is not detected in the second medical image or the situation in which the lesion candidate not detected in the first medical image is detected in the second medical image.

The difference between the first analysis result and the second analysis result includes the size or the range is different in a predetermined amount or more between the lesion candidate detected in the first medical image and the lesion candidate detected in the second medical image.

In the situation that there is the difference between the first analysis result and the second analysis result, the controller 31 outputs information showing that there is the difference. With this, an output is made in a manner different from output of the situation in which there is no difference. An example of "output of information showing that there is a difference" includes adding information showing that there is the difference and displaying the information.

Specifically, in the situation in which there is the difference between the first analysis result and the second analysis result, the controller 31 notifies the information showing that there is the difference to the user. In the situation in which there is no difference between the first analysis result and the second analysis result, the controller 31 does not notify the user. The notification of the information showing that there is the difference includes a notification by a pop-up window, a notification by e-mail, a notification by communication measures such as telephone, or the like.

For example, in the situation in which there is the difference between the first analysis result and the second analysis result, the controller 31 displays a pop-up window including the information showing that there is the difference on the display 33.

In the situation in which there is the difference between the first analysis result and the second analysis result, the controller 31 transmits a request to acquire the e-mail address corresponding to the person who interprets the first medical image to the medical image management server 10 through the communicator 34. The person who interprets the first medical image may be a user who selected the first medical image as the target of interpretation on the information processing apparatus 30 or the user specified in the information processing apparatus 30 as the person who interprets the first medical image. The controller 11 of the medical image management server 10 reads the e-mail address corresponding to the person who interprets the first medical image from the user management table 141 of the storage 14, and transmits the e-mail address to the information processing apparatus 30 through the communicator 12. The controller 31 of the information processing apparatus 30 acquires the e-mail address corresponding to the person who interprets the first medical image from the medical image management server 10 and transmits e-mail including information showing that there is the difference to this e-mail address through the communicator 34.

In the situation in which there is the difference between the first analysis result and the second analysis result, the controller 31 transmits a request to acquire the telephone number corresponding to the person who interprets the first medical image to the medical image management server 10 through the communicator 34. The controller 11 of the medical image management server 10 reads the telephone number corresponding to the person who interprets the first medical image from the user management table 141 of the storage 14, and transmits the telephone number to the information processing apparatus 30 through the communicator 12. The controller 31 of the information processing apparatus 30 acquires the telephone number corresponding to the person who interprets the first medical image from the medical image management server 10 and performs a process to make a call based on voice data including information showing that there is the difference to this telephone number.

The notification by e-mail or telephone regarding the information showing that there is the difference may be performed on the medical image management server 10 side.

In the situation in which there is the difference between the first analysis result and the second analysis result, the controller 31 changes the manner that a mouse cursor is displayed. With this, an output is made in a manner different from output of the situation in which there is no difference. Specifically, in the situation in which there is the difference between the first analysis result and the second analysis result, the controller 31 displays the color, shape, etc. of the mouse cursor on the display screen of the medical image differently from the situation in which there is no difference (normal situation). In the situation in which there is no difference between the first analysis result and the second analysis result, the controller 31 displays the mouse cursor in a usual manner (color, shape, etc. in the default state).

In the situation that there is the difference between the first analysis result and the second analysis result, the controller 31 changes the manner that a window is displayed. With this, an output is made in a manner different from output of the situation in which there is no difference. The window is the display region of the application. For example, a display region of the application to display the medical image and the analysis result is used as the window in which the manner of display is changed. Examples of the change in the manner of display of the window include, changing a frame of the window (color, type, etc.), changing the color of the region that is the background with relation to the medical image display region, and the like. A tool display region in the window is included in the region that is the background. In the situation in which there is no difference between the first analysis result and the second analysis result, the controller 31 displays the widow in a usual manner (state in the default state).

In the situation in which there is the difference between the first analysis result and the second analysis result, the controller 31 displays with highlight the portion in which there is the difference between the first analysis result and the second analysis result. With this, an output is made in a manner different from output of the situation in which there is no difference. The display with emphasis is to change or add at least one of the color, shape, letter, and/or the mark in the portion in which there is the difference between the first analysis result and the second analysis result and to display the result.

To display with highlight the portion in which there is the difference means to display the information included in the first analysis result but not included in the second analysis result or the information not included in the first analysis result but included in the second analysis result in a manner different from the portion in which there is no difference.

Specifically, in the situation that there is the difference between the first analysis result and the second analysis result, the controller 31 displays with highlight the portion in which there is the difference in the first analysis result compared to the second analysis result on the display screen of the first medical image. On the other hand, in the situation in which there is no difference between the first analysis result and the second analysis result, the manner of display of the display screen of the first medical image is displayed as usual (for example, state in which the first analysis result is displayed overlapped on the first medical image).

In the situation that there is the difference between the first analysis result and the second analysis result, the controller 31 displays only the portion in which there is the difference between the first analysis result and the second analysis result. With this, an output is made in a manner different from output of the situation in which there is no difference. For example, in the situation in which there is the difference between the first analysis result and the second analysis result, the controller 31 displays only the portion in which there is the difference between the first analysis result and the second analysis result overlapped on the first medical image in the display screen of the first medical image. The controller 31 does not display the portion in which there is no difference between the first analysis result and the second analysis result.

[Operation of Medical Image Display System]

Next, the operation of the medical image display system 100 is described.

Figure 5:
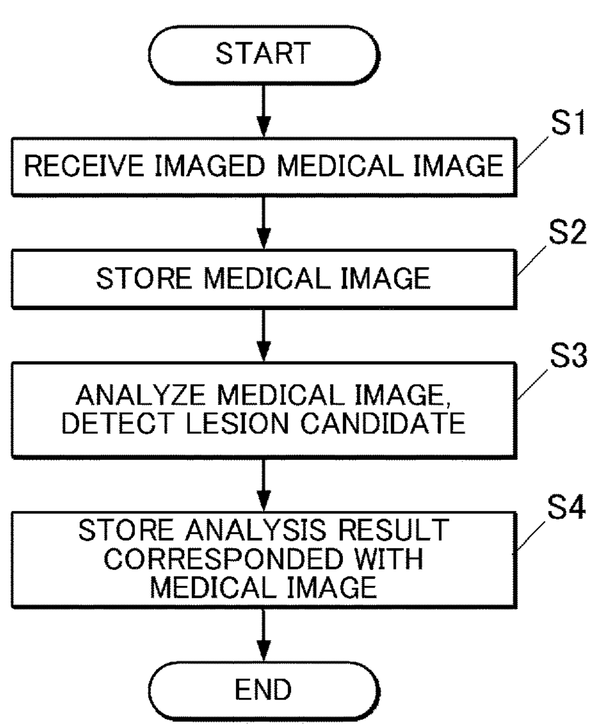
FIG. 5 is a flowchart showing a medical image analysis process performed by a medical image management server.

FIG. 5 is a flowchart showing a medical image analysis process performed by the medical image management server 10. This process is realized by software processing that is performed by the CPU of the controller 11 in coordination with a program stored in the storage 14.

When the medical image management server 10 receives the medical image obtained by imaging the patient from the modality 20 through the communicator 12 (step S1), the controller 11 stores the received medical image in the medical image storage region 143 of the storage 14 (step S2). The controller 11 stores the image ID, the patient ID, the imaged date/time, the modality, the site, the direction, and the like included in the supplementary information of the received medical image in the data management table 142 (see FIG. 3) of the storage 14 in a corresponded state.

Next, the controller 11 analyzes the medical image with a CAD function of the image analyzer 13 (step S3). The image analyzer 13 analyzes the medical image with an AI (Artificial Intelligence) and generates the data of the analysis result. Specifically, the image analyzer 13 detects the lesion candidate from the medical image and generates the analysis result including the position, size, type, etc. of the lesion candidate.

The position of the candidate lesion included in the analysis result is specified with a point, circle, ellipse, etc.

(1) Situation Specified by a Point (POINT)

Figure 6A:
FIG. 6A is an example in which a position of a lesion candidate is specified by a point on the medical image.

In the situation in which the position of the lesion candidate on the medical image is specified by a point, as shown in FIG. 6A, a position of a point P1 (coordinate in a vertical direction, coordinate in a horizontal direction) which is a center of the lesion candidate is specified. In such situation, the size and the range of the lesion candidate is not specified, and the annotation (circle, quadrilateral, etc.) displayed in the position of the lesion candidate on the display screen of the medical image depends on the viewer.

(2) Situation Specified by a Circle (CIRCLE)

Figure 6B:
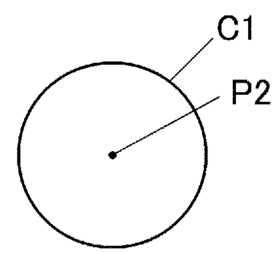
FIG. 6B is an example in which a position of a lesion candidate is specified by a circle on the medical image.

In the situation in which the position of the lesion candidate on the medical image is specified by a circle, as shown in FIG. 6B, a position of a point P2 (coordinate in a vertical direction, coordinate in a horizontal direction) which is a center pixel of the circle Cl and positions of pixels on a circumference of the circle Cl (coordinate in a vertical direction, coordinate in a horizontal direction) are specified.

(3) Situation Specified by an Ellipse (ELLIPSE)

Figure 6C:
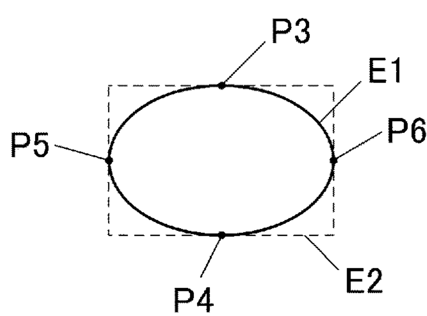
FIG. 6C is an example in which a position of a lesion candidate is specified by an ellipse on the medical image.

In the situation in which the position of the lesion candidate on the medical image is specified by an ellipse, as shown in FIG. 6C, positions of four points P3 to P6 (coordinate in a vertical direction, coordinate in a horizontal direction) which are points where each side of a minimum rectangle E2 surrounding the ellipse E1 come into contact with the ellipse E1 are specified.

Next, the controller 11 stores the analysis result obtained by the image analyzer 13 corresponded with the medical image in the storage 14 (step S4). Specifically, the controller 11 stores the analysis result in the analysis result storage region 144 of the storage 14 and stores the analysis result ID of the analysis result in the record corresponding to the medical image that is the target of analysis in the data management table 142 of the storage 14.

With this, the medical image analysis process ends.

As described above, the image analyzer 13 of the medical image management server 10 performs the computer process on the first medical image of the patient and functions as the first generator that generates the first analysis result. The image analyzer 13 may perform the computer process on the second medical image in which the same patient as the first medical image is imaged, and may function as the second generator that generates the second analysis result.

Figure 7:
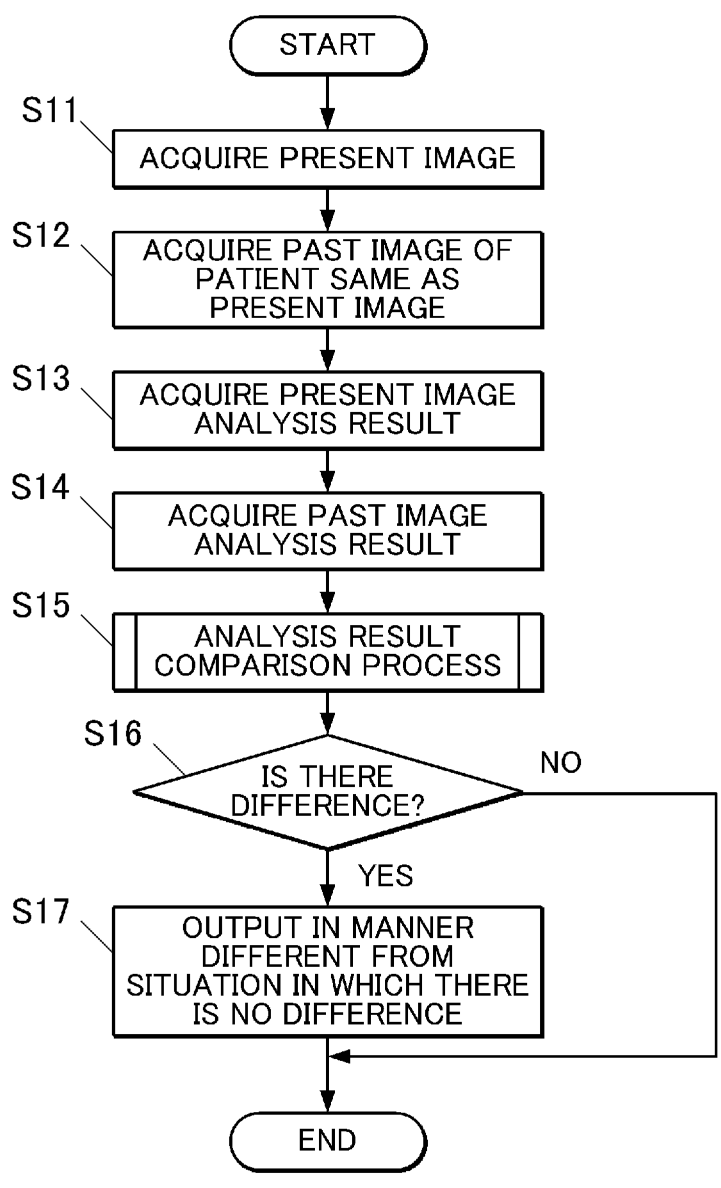
FIG. 7 is a flowchart showing an analysis result output process performed by the information processing apparatus.

FIG. 7 is a flowchart showing an analysis result output process performed by the information processing apparatus 30. This process is realized by software processing that is performed by the CPU of the controller 31 in coordination with the analysis result output process program 351 stored in the storage 35.

In the situation in which the user (physician) accesses to the medical image management server 10 from the information processing apparatus 30, when the user inputs the user ID and the password by operation on the operator 32, the controller 31 transmits the input user ID and password to the medical image management server 10 through the communicator 34.

In the medical image management server 10, when the user ID and the password is received by the communicator 12, the controller 11 determines whether the received user ID and the password matches with any combination of the user ID and the password registered in advance in the user management table 141 of the storage 14. When it is determined that there is a match, the user is authorized to use the information processing apparatus 30.

The controller 31 of the information processing apparatus 30 acquires the present image from the medical image management server 10 through the communicator 34 (step S11). For example, the controller 31 transmits the request to acquire the medical image including the image ID specified by the operation on the operator 32 by the user to the medical image management server 10 through the communicator 34. The controller 11 of the medical image management server 10 reads the medical image corresponding to the image ID included in the acquiring request from the medical image storage region 143 and transmits the medical image to the information processing apparatus 30 through the communicator 12.

The controller 31 of the information processing apparatus 30 may acquire the present image from the modality 20.

Next, the controller 31 of the information processing apparatus 30 acquires the past image imaging the same patient as the present image from the medical image management server 10 through the communicator 34 (step S12). For example, the controller 31 transmits the acquiring request of the past image including the image ID of the present image to the medical image management server 10 through the communicator 34. The controller 11 of the medical image management server 10 refers to the data management table 142 of the storage 14. The controller 11 extracts the record that has the "patient ID", "modality", "site" and "direction" the same as the present image, that has an "imaged date/time" before the present image and that is the most recent record. The controller 11 specifies the image ID (image ID of the past image) included in the extracted record. The controller 11 reads the medical image corresponding to the image ID of the past image from the medical image storage region 143 and transmits the medical image to the information processing apparatus 30 through the communicator 12.

The conditions used to specify the past image are not limited to the above examples.

Next, the controller 31 of the information processing apparatus 30 acquires the present image analysis result from the medical image management server 10 through the communicator 34 (step S13). For example, the controller 31 transmits the request to acquire the present image analysis result to the medical image management server 10 through the communicator 34. The controller 11 of the medical image management server 10 refers to the data management table 142 of the storage 14. The controller 11 specifies the "analysis result ID" from the record corresponding to the "image ID" of the present image, reads the analysis result corresponding to the "analysis result ID" from the analysis result storage region 144, and transmits the analysis result to the information processing apparatus 30 through the communicator 12.

Next, the controller 31 of the information processing apparatus 30 acquires the past image analysis result from the medical image management server 10 through the communicator 34 (step S14). For example, the controller 31 transmits the request to acquire the past image analysis result to the medical image management server 10 through the communicator 34. The controller 11 of the medical image management server 10 refers to the data management table 142 of the storage 14. The controller 11 specifies the "analysis result ID" from the record corresponding to the "image ID" of the past image, reads the analysis result corresponding to the "analysis result ID" from the analysis result storage region 144, and transmits the analysis result to the information processing apparatus 30 through the communicator 12.

Next, the controller 31 of the information processing apparatus 30 performs the analysis result comparison process (step S15). The analysis result comparison process is a process to compare the present image analysis result with the past image analysis result.

Figure 8:
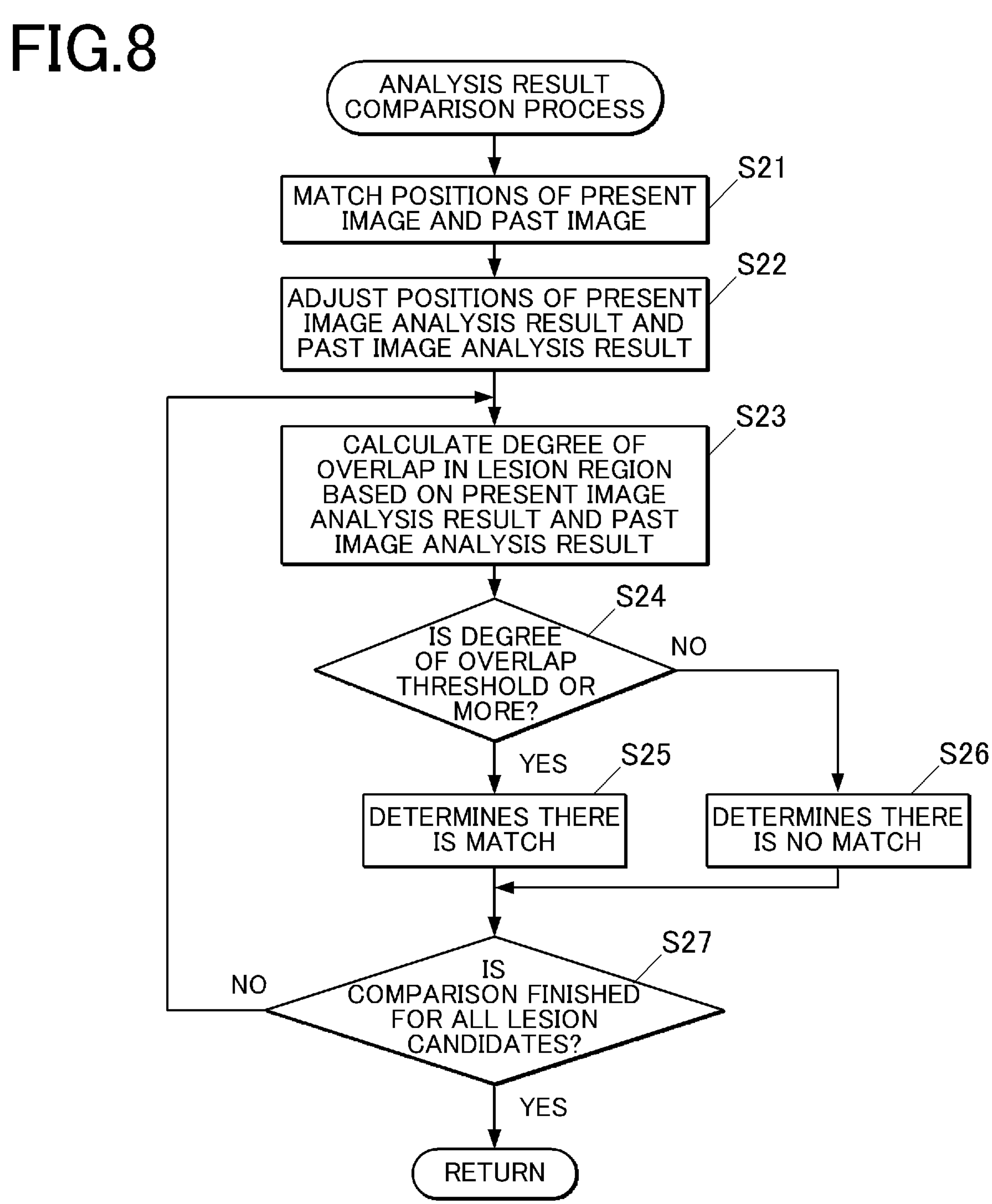
FIG. 8 is a flowchart showing an analysis result comparison process.

The analysis result comparison process is described with reference to FIG. 8.

The controller 31 of the information processing apparatus 30 matches the positions of the present image and the past image (step S21). Specifically, the controller 31 performs the enlarging/reducing/rotating process on both or either one of the present image and/or the past image, and matches the positions of the bones, organs, etc. in the image between the present image and the past image.

Next, the controller 31 adjusts the positions between the present image analysis result and the past image analysis result in view of the alignment of the present image and the past image (step S22). Specifically, the controller 31 converts the position of the lesion candidate included in the present image analysis result or the past image analysis result to the position after the alignment of the images.

Next, the controller 31 calculates the degree of overlap in the lesion candidate for a certain lesion candidate based on the present image analysis result and the past image analysis result after adjusting the position (step S23). For example, as the degree of overlap of the lesion region, a percentage of an "overlapping region of the lesion region in the present image and the lesion region in the past image" with relation to the "lesion region in the past image" is used.

The overlapping degree of the lesion region is to be 0 for the lesion candidate existing in only either one between the present image analysis result and the past image analysis result.

In the situation in which the position of the lesion candidate is specified by one point (center position) in the analysis result (see FIG. 6A), the controller 31 calculates the percentage (overlapping degree) that the regions overlap in the range (for example, circle of a predetermined radius) specified in advance from a lesion center position in the present image analysis result and the past image analysis result. Here, the range specified in advance can be changed for each medical facility (medical facility that performs imaging, medical facility to where the user belongs, etc.), department making the request (department to where the physician requesting the imaging or the interpretation belongs), imaging site, and the like. The user (physician) may specify any value as the range specified in advance. The value of the range specified in advance can be changed between the upper part and the lower part of the medical image. For example, in the situation of a chest image, since the position of a diaphragm changes according to breathing of the patient, even if the same lesion is imaged, the position of the lesion in the vertical direction may greatly change in the lower part compared to the upper part of the chest image depending on the timing that the lesion is imaged.

In the situation in which the position of the lesion candidate is specified by a circle in the analysis result (see FIG. 6B), the controller 31 calculates the percentage (overlapping degree) of the overlap between the circles showing the position of the lesion candidate in the present image analysis result and the past image analysis result.

In the situation in which the position of the lesion candidate is specified by an ellipse in the analysis result (see FIG. 6C), the controller 31 calculates the percentage (overlapping degree) of the overlap between the ellipses showing the position of the lesion candidate in the present image analysis result and the past image analysis result.

Next, the controller 31 determines whether the overlapping degree of the lesion region in the present image analysis result and the past image analysis result is equal to or greater than a threshold set in advance (step S24). According to such threshold, it is possible to detect not only the difference showing whether the lesion candidate exists in both images but also the difference showing that the size and the range of the lesion candidate changed in an amount equal to or larger than a predetermined amount in both images. The threshold used here can be changed according to the medical facility, requesting department, the imaged site, and the user. A value of the threshold can be different between the upper part and the lower part of the medical image.

If the overlapping degree of the lesion region in the present image and the past image is equal to or larger than the threshold (step S24; YES), the controller 31 determines that the lesion candidate detected from the present image matches with the lesion candidate detected from the past image (step S25).

In step S24, if the overlapping degree of the lesion region in the present image and the past image is less than the threshold (step S24; NO), the controller 31 determines that the lesion candidate detected from the present image does not match with the lesion candidate detected from the past image (step S26).

After step S25 or step S26, the controller 31 determines whether the comparison for all lesion candidates included in the present image analysis result and the past image analysis result is finished (step S27).

If there are still lesion candidates with which the comparison is not finished (step S27: NO), the process returns to step S23, and the controller 31 repeats the process with a different lesion candidate as the target of the process.

In step S27, if the comparison for all lesion candidates is finished (step S27; YES), the analysis result comparison process ends.

Instead of the process using the overlapping degree in step S24, the controller 31 may determine that the lesion candidate detected from the present image does not match with the lesion candidate detected from the past image (there is a large change) if the difference in the size (length, square area, etc.) of the lesion candidate is equal to or larger than a predetermined amount between the present image analysis result and the past image analysis result. Alternatively, the controller 31 may determine that the lesion candidate detected from the present image does not match with the lesion candidate detected from the past image (there is a large change) if the difference in the range (square area of non-overlapping region, etc.) of the lesion candidate is equal to or larger than a predetermined amount between the present image analysis result and the past image analysis result.

Figure 9:
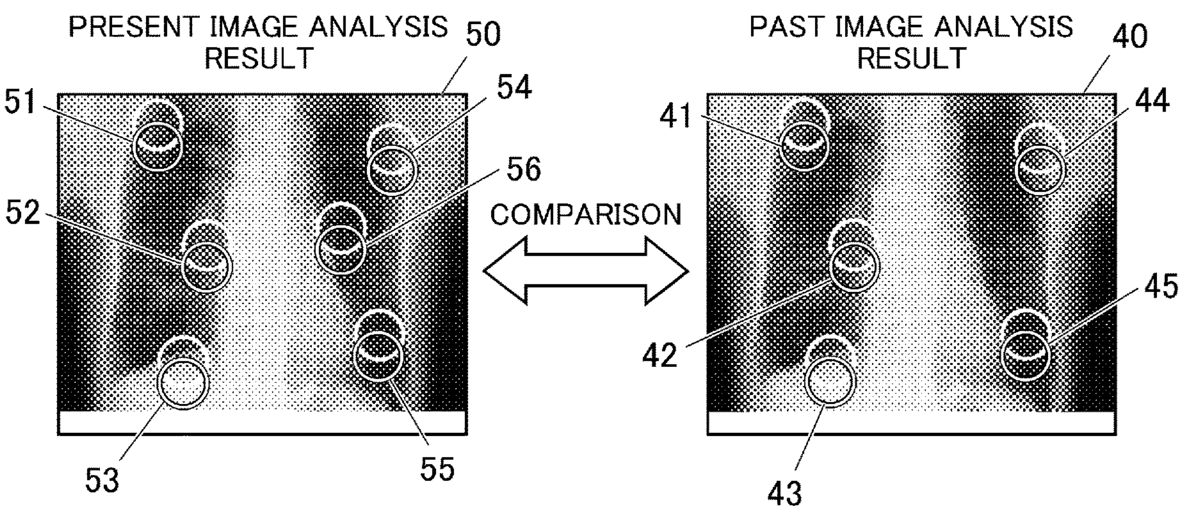
FIG. 9 is an image showing a comparison between a past image analysis result and a present image analysis result.

FIG. 9 is an image showing a comparison between a past image analysis result 40 and a present image analysis result 50. In the example shown in FIG. 9, five lesion candidates 41 to 45 are included in the past image analysis result 40 whereas six lesion candidates 51 to 56 are included in the present image analysis result 50. The lesion candidates 51 to 55 included in the present image analysis result 50 are considered to correspond to (to be the same lesion as) the lesion candidates 41 to 45 included in the past image analysis result 40, respectively. The present image analysis result 50 includes the newly detected lesion candidate 56.

After the analysis result comparison process, returning to FIG. 7, the controller 31 of the information processing apparatus 30 determines whether there is the difference between the present image analysis result and the past image analysis result (step S16). Specifically, the controller 31 determines that there is the difference in the situation in which there is a lesion candidate that is determined to not match between the present image analysis result and the past image analysis result. On the other hand, the controller 31 determines that there is no difference in the situation in which it is determined that all lesion candidates match between the present image analysis result and the past image analysis result.

In the situation in which there is the difference between the present image analysis result and the past image analysis result (step S16; YES), the controller 31 of the information processing apparatus 30 makes an output in a manner different from the situation in which there is no difference (step S17). For example, when the controller 31 displays on the display 33 the present image and the present image analysis result, a display according to the later-described output example is performed.

After step S17, or in the situation in which there is no difference between the present image analysis result and the past image analysis result in step S16 (step S16; NO), the analysis result output process ends.

Below, the specific output examples A to I in step S17 of the analysis result output process (see FIG. 7) is described. In the output examples A to I, the present image analysis result 50 and the past image analysis result 40 shown in FIG. 9 are used. The output examples A to D (see FIG. 10 to FIG. 13) are examples showing that there is the difference between the present image analysis result and the past image analysis result. The output examples E to H (see FIG. 14 to FIG. 17) are examples displaying with highlight the portions that are different between the present image analysis result and the past image analysis result. The output example I (see FIG. 18) is an example displaying only the portion in which there is the difference between the present image analysis result and the past image analysis result.

Output Example A

In the situation in which there is the difference between the present image analysis result and the past image analysis result, the controller 31 of the information processing apparatus 30 displays on the display 33 a message to notify that there is the difference between the above.

Figure 10:
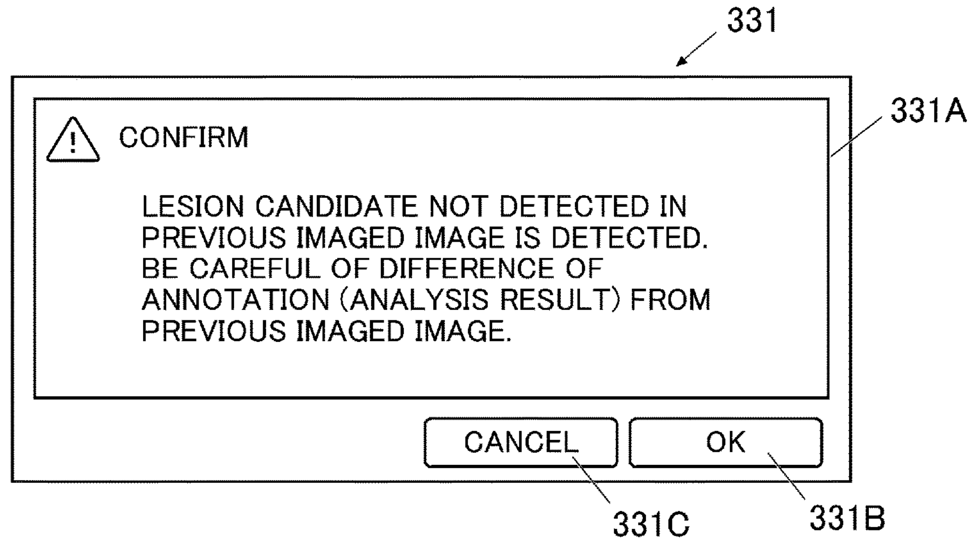
FIG. 10 is an example of a pop-up window in output example A.

FIG. 10 shows an example of a pop-up window 331 displayed on the display 33. The pop-up window 331 is displayed on an interpretation screen of the present image (screen in which the present image analysis result is overlapped on the present image), for example. The pop-up window 331 includes a message display region 331A, an OK button 331B, and a cancel button 331C.

The message display region 331A displays a message showing that a lesion candidate which is not detected from the past image (previous imaged image) is detected in the present image (imaged image this time).

The OK button 331B is a button to perform an operation to indicate that the user confirmed that there is the difference between the present image analysis result and the past image analysis result. If the user operates the operator 32 and presses the OK button 331B, the controller 31 displays on the display 33 the present image in which the present image analysis result (annotation) is overlapped side by side with the past image in which the past image analysis result is overlapped (comparison interpretation screen).

The cancel button 331C is a button to perform an operation to indicate that, after the user confirms that there is the difference between the present image analysis result and the past image analysis result, the user will continue the interpretation of the present image. If the user operates the operator 32 and presses the cancel button 331C, the controller 31 does not display the pop-up window 331, and continues to display only the present image in which the present image analysis result is overlapped.

The controller 31 does not notify the message as shown in FIG. 10 in the situation in which there is no difference between the present image analysis result and the past image analysis result.

Output Example B

In the situation in which there is the difference between the present image analysis result and the past image analysis result, the controller 31 of the information processing apparatus 30 changes the manner of display of the mouse cursor to be different from the normal manner of display.

Figure 11:
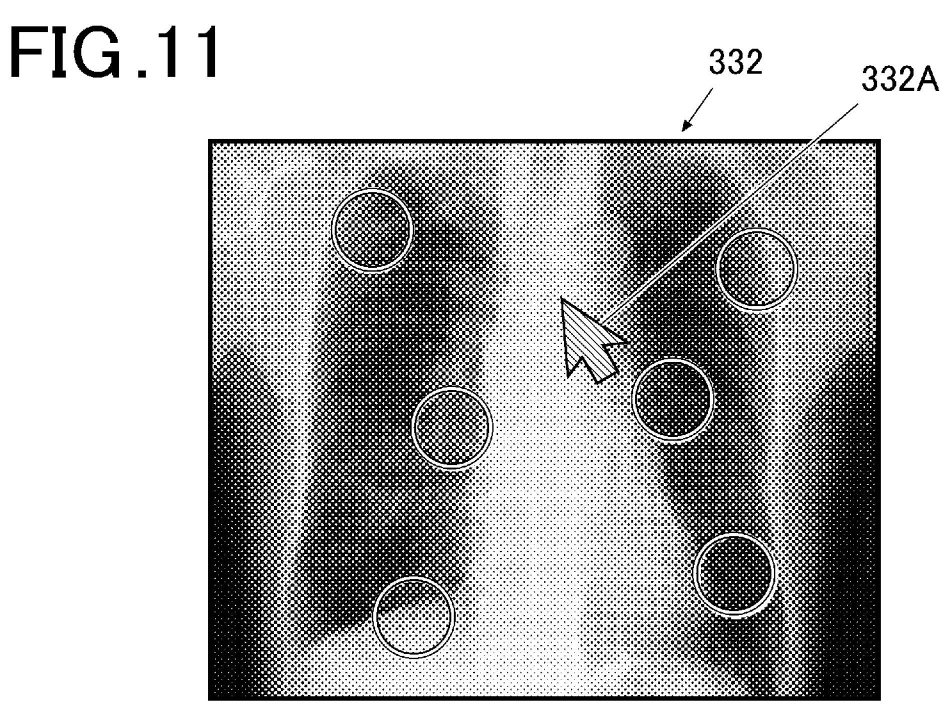
FIG. 11 is an example of an interpretation screen in output example B.

FIG. 11 shows an example of an interpretation screen 332 displayed on the display 33. The present image analysis result is displayed overlapped on the present image in the interpretation screen 332. The mouse cursor 332A on the interpretation screen 332 has a different color compared to the normal situation. The shape of the mouse cursor 332A may also be changed.

The controller 31 does not change the manner of display of the mouse cursor in the situation in which there is no difference between the present image analysis result and the past image analysis result.

Output Example C

In the situation in which there is the difference between the present image analysis result and the past image analysis result, the controller 31 of the information processing apparatus 30 changes the manner of display of the window to be different from the normal manner of display.

Figure 12:
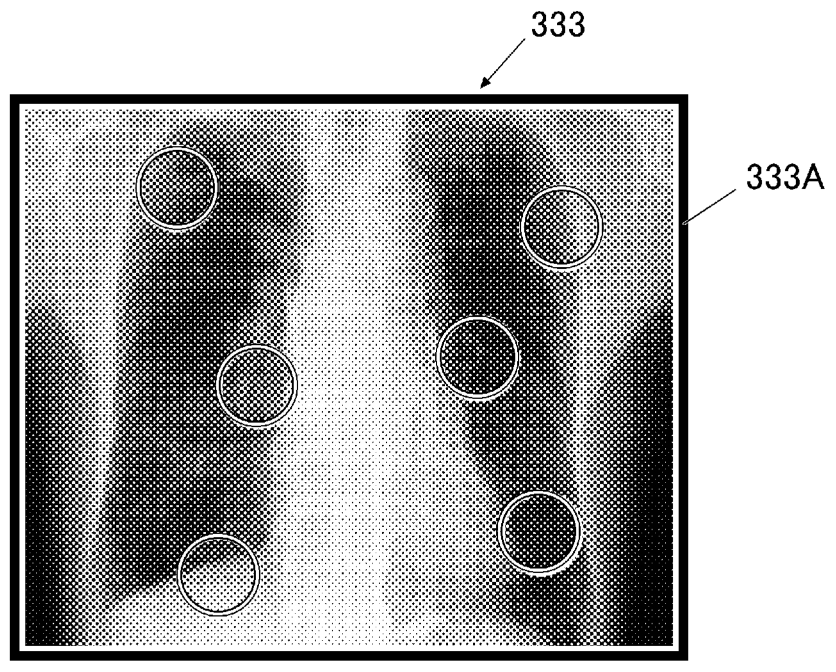
FIG. 12 is an example of an interpretation screen in output example C.

FIG. 12 shows an example of an interpretation screen 333 displayed on the display 33. The present image analysis result is displayed overlapped on the present image in the interpretation screen 333. A window frame 333A of the interpretation screen 333 has a different color compared to the normal situation.

The controller 31 does not change the manner of display of the window in the situation in which there is no difference between the present image analysis result and the past image analysis result.

Output Example D

Similar to the output example C, the output example D is also an example of the situation in which a notification is made that there is the difference between the present image analysis result and the past image analysis result by changing the manner of display of the window.

Figure 13A:
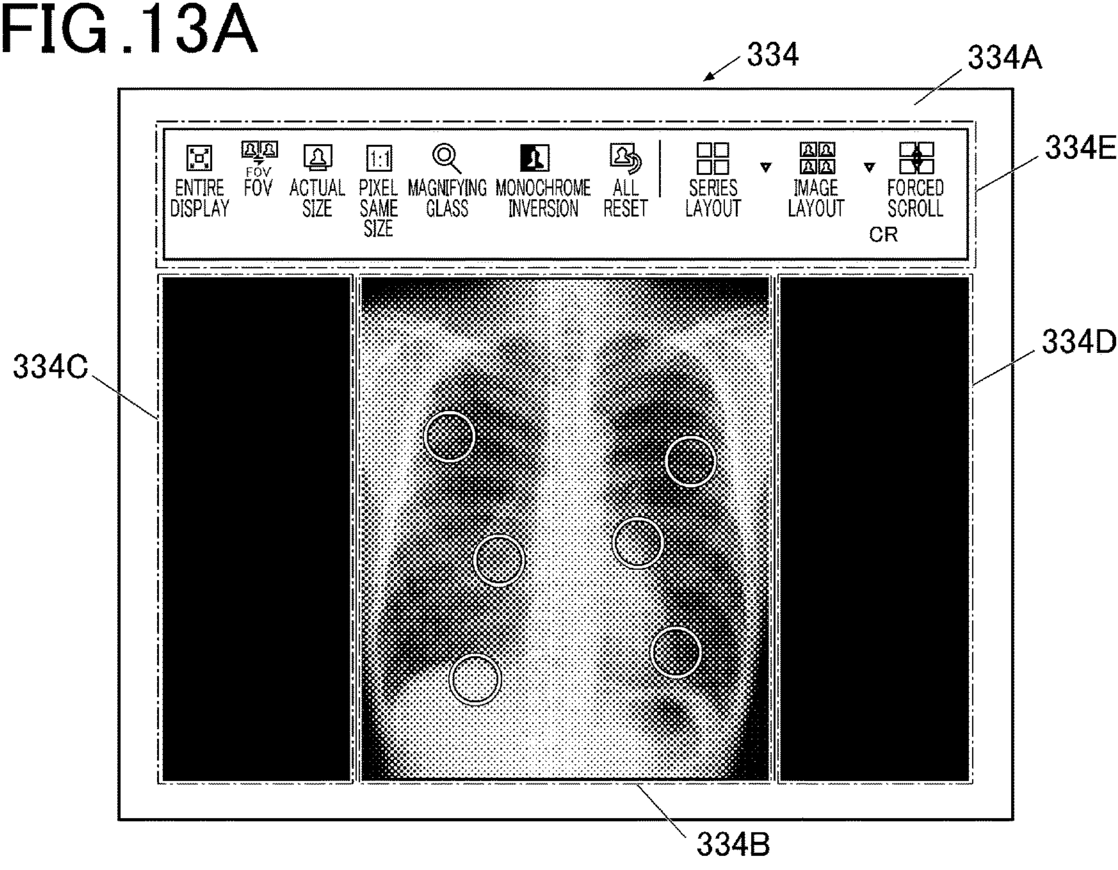
FIG. 13A is an example of an interpretation screen in the situation in which there is no difference between the present image analysis result and the past image analysis result.
Figure 13B:
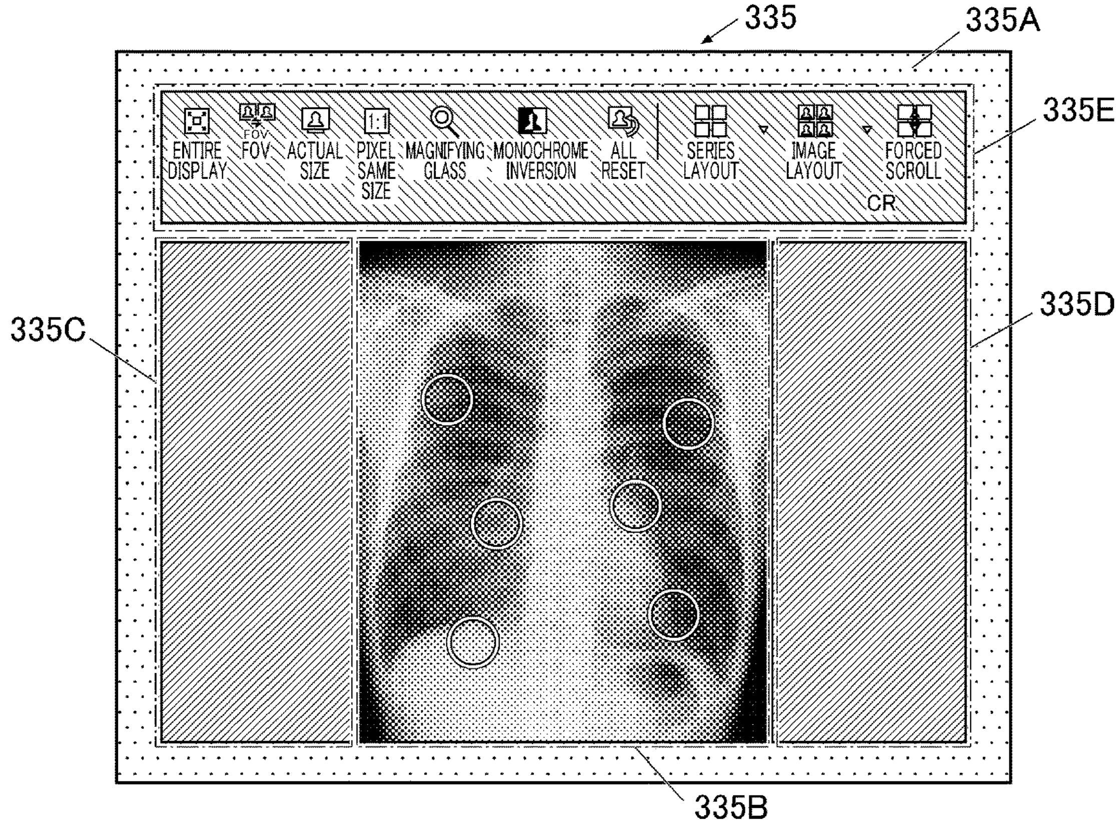
FIG. 13B is an example of an interpretation screen in the situation in which there is a difference between the present image analysis result and the past image analysis result in output example D.

FIG. 13A shows an example of an interpretation screen 334 in the situation in which there is no difference between the present image analysis result and the past image analysis result, and FIG. 13B shows an example of an interpretation screen 335 in the situation in which there is the difference between the present image analysis result and the past image analysis result.

As shown in FIG. 13A, the interpretation screen 334 in the situation in which there is no difference includes, a window frame 334A, a medical image display region 334B, image outside regions 334C and 334D, and a tool display region 334E. The present image analysis result is displayed overlapped on the present image in the medical image display region 334B. The image outside regions 334C and 334D are regions which are to be the background of the medical image display region 334B. Tool selection buttons to select the process to be performed on the medical image are displayed in the tool display region 334E. The tool display region 334E is a portion of the region which is to be the background of the medical image display region 334B.

As shown in FIG. 13B, the interpretation screen 335 in the situation in which there is the difference includes, a window frame 335A, a medical image display region 335B, image outside regions 335C and 335D, and a tool display region 335E. The window frame 335A, the medical image display region 335B, the image outside regions 335C and 335D, and a tool display region 335E are the same as the window frame 334A, the medical image display region 334B, the image outside regions 334C and 334E, and the tool display region 334E in the interpretation screen 334, respectively.

Compared to FIG. 13A, in FIG. 13B, the color of the window frame 335A is changed, and the color of the region which is to be the background in the medical image display region 335B (image outside regions 335C and 335D and tool display region 335E) is changed. With this, in the situation in which there is the difference between the present image analysis result and the past image analysis result, it is possible to urge the user to pay attention to the present image analysis result.

Output Example E

In the situation in which there is the difference between the present image analysis result and the past image analysis result, the controller 31 of the information processing apparatus 30 displays with highlight the portion in which there is the difference between the present image analysis result and the past image analysis result. Specifically, it is preferable that the controller 31 displays the lesion candidate newly presented in the present analysis result with more emphasis than the previous analysis result of the interpretation target patient. The same can be said for output examples F to H.

In the situation in which there is no difference between the present image analysis result and the past image analysis result, the controller 31 performs the display in a normal manner of display.

Figure 14:
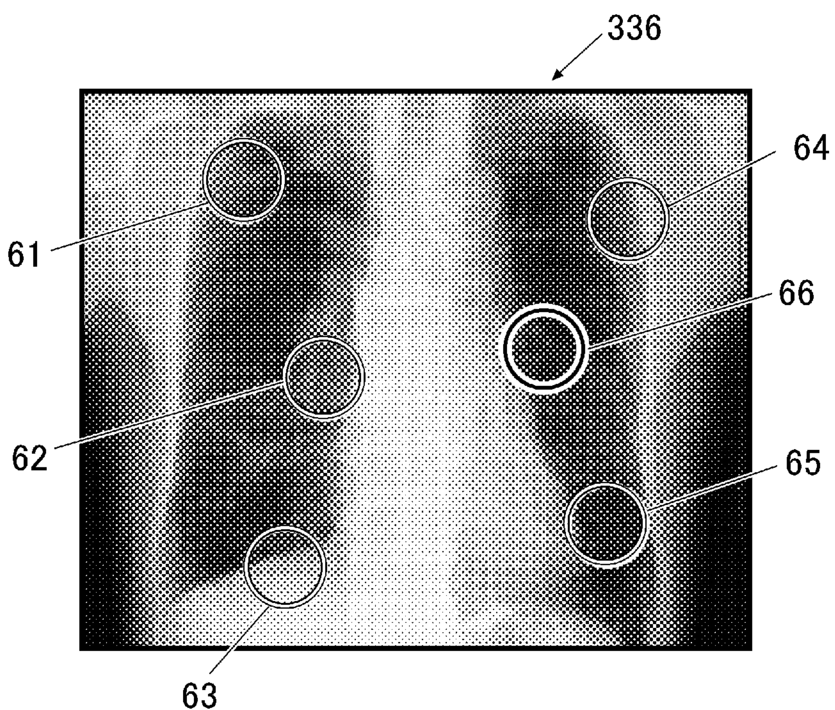
FIG. 14 is an example of an interpretation screen in output example E.

FIG. 14 shows an example of an interpretation screen 336 displayed on the display 33. The present image analysis result is displayed overlapped on the present image in the interpretation screen 336. In the interpretation screen 336, the color of an annotation 66 corresponding to the lesion candidate which was not detected in the past image analysis result is represented by the color different from the other annotations 61 to 65. With this, the portion that is different between the present image analysis result and the past image analysis result is displayed with highlight.

In addition to the lesion candidate newly presented in the present image analysis result, the lesion candidate which greatly changed from the past image analysis result to the present image analysis result (considered to be the same lesion but the size and range changed a predetermined amount or more) is also displayed with highlight as the different portion. The lesion candidate which was detected from the past image but which is not detected in the present image may be displayed with highlight as a different portion on the past image or may be displayed with highlight as the different portion on a comparison interpretation screen including the past image and the present image.

Output Example F

Figure 15:
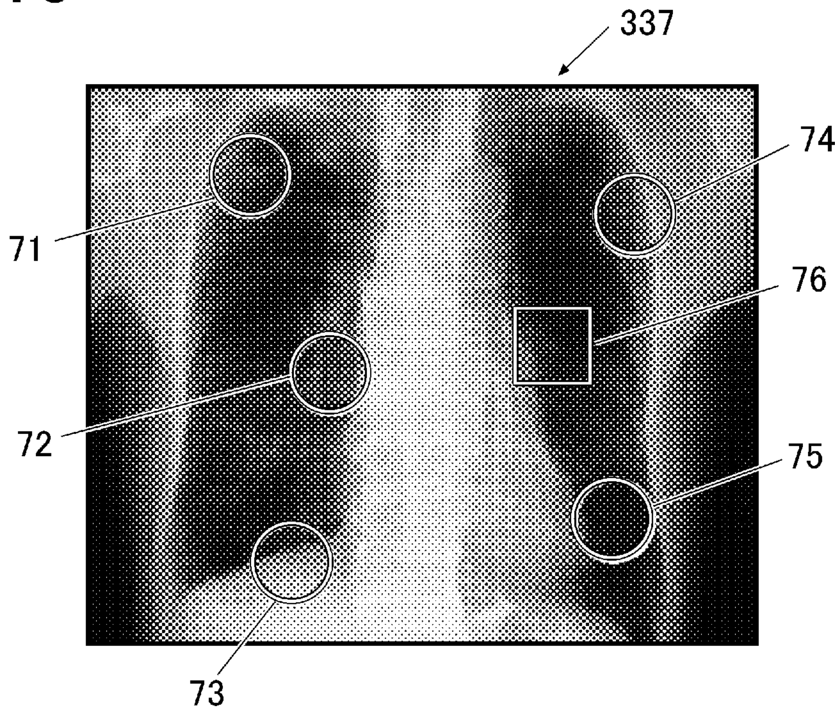
FIG. 15 is an example of an interpretation screen in output example F.

FIG. 15 shows an example of an interpretation screen 337 displayed on the display 33. The present image analysis result is displayed overlapped on the present image in the interpretation screen 337. In the interpretation screen 337, the shape of an annotation 76 (square in FIG. 15) corresponding to the lesion candidate which was not detected in the past image analysis result is represented by the shape different from the other annotations 71 to 75 (circle in FIG. 15). With this, the portion that is different between the present image analysis result and the past image analysis result is displayed with highlight.

Output Example G

Figure 16:
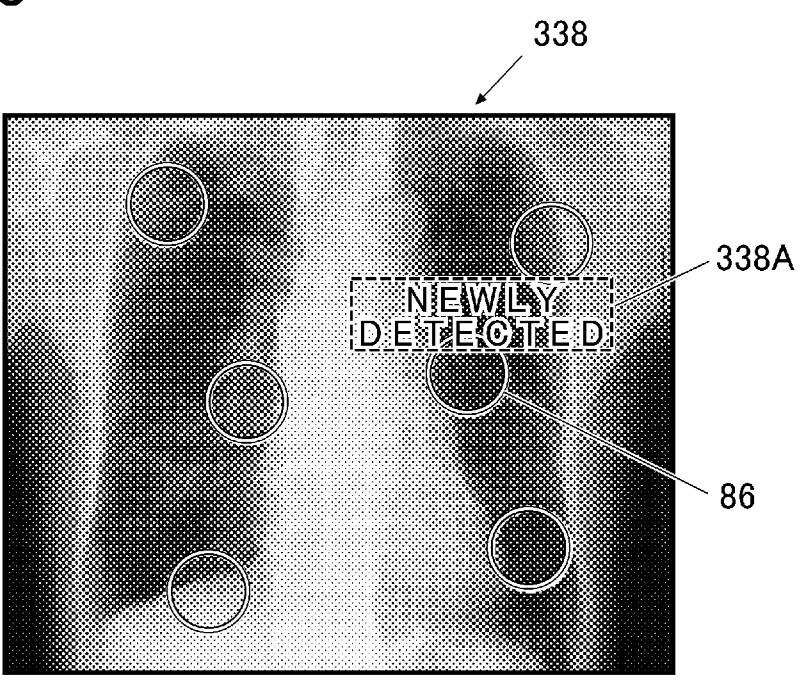
FIG. 16 is an example of an interpretation screen in output example G.

FIG. 16 shows an example of an interpretation screen 338 displayed on the display 33. The present image analysis result is displayed overlapped on the present image in the interpretation screen 338. In the interpretation screen 338, letters 338A showing “NEWLY DETECTED” is added near an annotation 86 corresponding to the lesion candidate which was not detected in the past image analysis result.

With this, the portion that is different between the present image analysis result and the past image analysis result is displayed with highlight.

Output Example H

Figure 17:
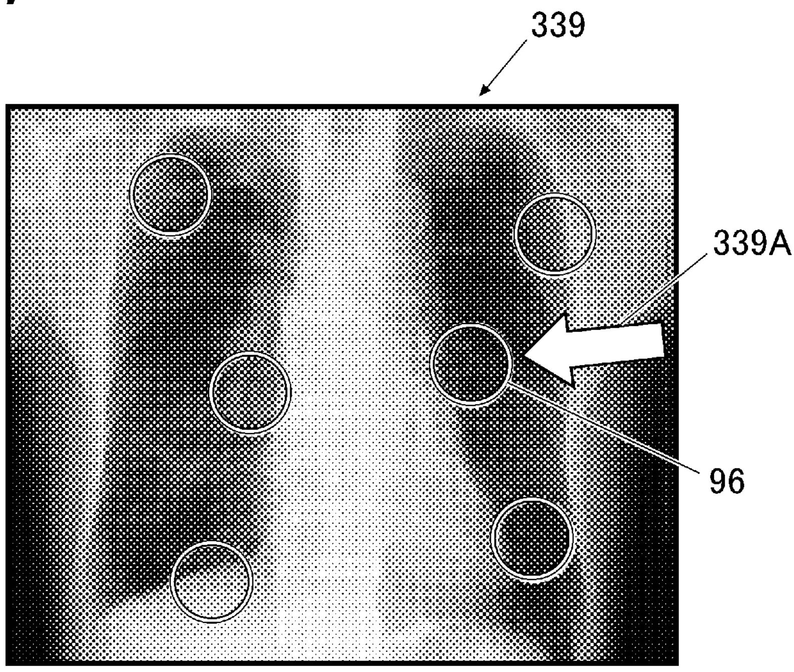
FIG. 17 is an example of an interpretation screen in output example H.

FIG. 17 shows an example of an interpretation screen 339 displayed on the display 33. The present image analysis result is displayed overlapped on the present image in the interpretation screen 339. Further, in the interpretation screen 339, a mark 339A is added near an annotation 96 corresponding to the lesion candidate which was not detected in the past image analysis result. With this, the portion that is different between the present image analysis result and the past image analysis result is displayed with highlight.

Output Example I

In the situation in which there is the difference between the present image analysis result and the past image analysis result, the controller 31 of the information processing apparatus 30 only displays the portion in which there is the difference between the present image analysis result and the past image analysis result.

In the situation in which there is no difference between the present image analysis result and the past image analysis result, the controller 31 displays the present image analysis result overlapped on the present image (normal display). Alternatively, in the situation in which there is no difference, the controller 31 does not display the analysis result on the present image.

Figure 18:
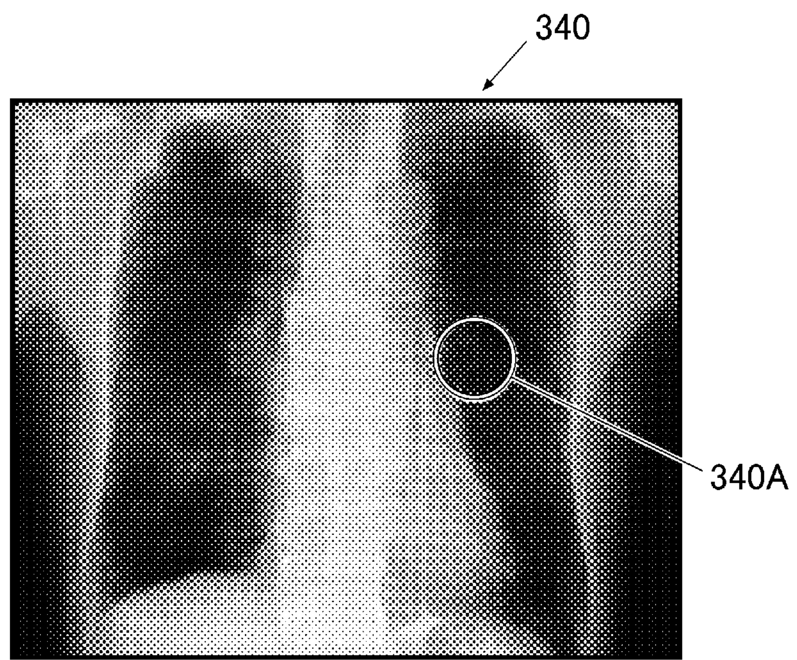
FIG. 18 is an example of an interpretation screen in output example I.

FIG. 18 shows an example of an interpretation screen 340 displayed on the display 33. The present image is displayed in the interpretation screen 340. Further, the annotation 340A corresponding to the lesion candidate that was not detected in the past image and that is detected in only the present image is displayed overlapped on the present image in the interpretation screen 340. On the other hand, an annotation showing a region with dashed lines, etc. is displayed overlapped on the present image to show the lesion candidate that was detected in the past image but that is not detected in the present image.

As described above, according to the present embodiment, in the situation in which the present image analysis result (first analysis result) and the past image analysis result (second analysis result) are compared and there is the difference between the above, the controller 31 of the information processing apparatus 30 performs the output in a manner different from the situation in which there is no difference. Therefore, it is possible to prevent overlooking the analysis result obtained by computer processing on the medical image.

For example, in the situation in which there is the difference between the present image analysis result and the past image analysis result, the controller 31 outputs the information showing that there is the difference. Therefore, it is possible to alert the user when the user interprets the present image while referring to the present image analysis result or compares and interprets the present image and the past image.

Specifically, it is possible to notify to the user the information showing that there is the difference by a pop-up window, e-mail, telephone, and the like.

In the situation in which there is the difference between the present image analysis result and the past image analysis result, the controller 31 is able to urge the user to pay attention to the analysis result by changing the manner of display of the mouse cursor.

In the situation in which there is the difference between the present image analysis result and the past image analysis result, the controller 31 is able to urge the user to pay attention to the analysis result by changing the manner of display of the window.

In addition, the controller 31 is able to point the user's attention to the location where there is a change from the past image to the present image by displaying with highlight the portion in which there is the difference between the present image analysis result and the past image analysis result. Specifically, the portion in which there is the difference can be shown in a manner that is easy to understand by changing the color, shape, etc. of the annotation of the portion in which there is the difference or adding letters, a mark, etc. to the portion in which there is the difference.

The controller 31 is able to point the user's attention to only the location in which there is a change from the past image to the present image by displaying only the portion in which there is the difference between the present image analysis result and the past image analysis result.

As described above, it is possible to display with highlight the portion in which there is the difference between the present image analysis result and the past image analysis result or to display only the portion in which there is the difference in order to make the portion in which it is assumed that the portion is not checked yet to stand out. With this, the user is able to efficiently understand the analysis result that should be checked with interest.

Moreover, in the situation in which the lesion candidate that is not detected in the past image is detected from the present image, in the situation in which the lesion candidate detected in the past image is not detected in the present image, and in the situation in which the size or the range of the lesion candidate is changed a predetermined amount or more from the lesion candidate detected in the past image to the lesion candidate detected in the present image, it is possible to determine that there is the difference between the present image analysis result and the past image analysis result.

The description of the embodiments are merely examples of the program, information processing apparatus, information processing method, and the information processing system according to the present invention, and the present invention is not limited to the above. The detailed configurations/components and operations of the components constituting the system can also be appropriately modified within the scope of the present invention.

For example, in step S17 of the analysis result output process (see FIG. 7), the output examples A to I may be combined and implemented.

Moreover, each of the output examples A to I may be corresponded to the modality 20 in advance, and the output example corresponded to the modality 20 with which the medical image as the processing target is generated may be applied.

In a state in which the medical image is displayed on the display 33 of the information processing apparatus 30, the applied output examples A to I may be switched each time the user presses a predetermined button on the operator 32.

Depending on the purpose of use of the display of the medical image and the analysis result, the output among the output examples A to I that is applied may be changed in the situation in which there is the difference between the first analysis result and the second analysis result. For example, for normal use, the display can be performed by changing the shape of the annotation 76 as in the output example F (see FIG. 15). For use in a conference, the mark 339A is attached to the portion in which there is the difference and displayed as in the output example H (see FIG. 17). For use in a report, only the annotation 340A showing the portion in which there is the difference is displayed as in the output example I (see FIG. 18).

In the situation in which there is no need for display of the analysis result in the output examples A to I, the analysis result may be hidden automatically. Examples in which there is no need to display the analysis result includes, the situation in which the annotation overlaps with measured lines such as cardiothoracic ratio, when a CINE (moving image) is played, or the like.

In the analysis result comparison process (see FIG. 8), in addition to determining "match" and "no match" of the lesion candidate in the present image analysis result and the past image analysis result, it is possible to discriminate among 3 or more levels such as "match", "possibility of no match", "no match" depending on the degree of overlapping in the lesion region.

Moreover, the display of the analysis result may be discriminated between "possibility of no match" and "no match" such as by changing the color of the annotation corresponding to the lesion candidate (for example, "no match" being "red", possibility of no match" being "blue", and the like).

According to the above described embodiment, the controller 31 of the information processing apparatus functions as the first acquirer, the second acquirer and the outputter, but the other apparatuses other than the information processing apparatus 30 may include units to perform the above functions.

According to the above embodiments, the medical image management server 10 is provided with the CAD function to perform the computer process on the medical image and to generate the analysis result (first generator, second generator), but apparatuses other than the medical image management server 10 may include the CAD function.

The above embodiments illustrate an example using the chest image as the medical image, but the imaged site is not limited to the chest portion. The medical image that is processed may be a plurality of slice images obtained by a CT, etc., multi-frame images (moving image), and images converting the image obtained by CT, MRI, etc. to 3D.

According to the above embodiments, the image data of the medical image and the data of the analysis result are stored in different regions (medical image storage region 143 and analysis result storage region 144) in the medical image management server 10. However, the data of the analysis result may be incorporated in the medical image file including the image data of the medical image.

According to the above embodiments, mainly, changing the manner of display on the display screen is described as the example of changing the manner of output in the situation in which there is the difference between the first analysis result and the second analysis result to be different from the situation in which there is no difference. Alternatively, display data may be output in order to display the manner of display of the situation in which there is the difference between the first analysis result and the second analysis result differently from the situation in which there is no difference. Moreover, print data may be output in order to print the situation in which there is the difference between the first analysis result and the second analysis result in a manner different from the situation in which there is no difference.

The first analysis result and the second analysis result are both uniformly generated according to the same rules by a computer process performed by the image analyzer 13 of the medical image management server 10. Therefore, the difference between the first analysis result and the second analysis result can be easily detected.

If the analysis result is obtained by the physician detecting the lesion candidate from the medical image and manually adding the annotation, even if the states of the lesion included in the first medical image and the second medical image are the same, it is difficult to add the annotations in the same position with the same size on both images. Therefore, the difference as in the originally intended meaning is difficult to detect between the analysis results generated manually or between the analysis result generated manually and the analysis result by computer processing.

Therefore, when the first analysis result is compared with the second analysis result, it is important to use the analysis result generated by computer processing.

The programs to execute the processes in the apparatuses may be stored in a portable storage medium. As the medium providing the data of the program through communication lines, a carrier wave can be applied.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A non-transitory computer-readable storage medium storing a program causing a computer to perform:

acquiring a first analysis result obtained by a computer process on a first medical image of a patient;

acquiring a second analysis result obtained by a computer process on a second medical image of the patient; and comparing the first analysis result and the second analysis result and in a situation in which there is a difference, outputting in a manner different from the situation in which there is no difference, wherein lesion candidates in the first analysis result and the second analysis result are specified with lesion regions, each of the lesion regions having a predetermined shape and size surrounding a center of a respective lesion candidate of the lesion candidates, and the comparing including determining a degree of overlap by calculating a percentage that the lesion regions of the first analysis result and the second analysis result overlap.

2. The storage medium storing the program according to claim 1, wherein, in the outputting, in the situation in which there is the difference, output is made in a manner different from the situation in which there is no difference by outputting information showing that there is the difference.

3. The storage medium storing the program according to claim 2, wherein, in the outputting, the information showing that there is the difference is notified to a user.

4. The storage medium storing the program according to claim 1, wherein, in the outputting, in the situation in which there is the difference, output is made in a manner different from the situation in which there is no difference by changing a manner of display of a mouse cursor.

5. The storage medium storing the program according to claim 1, wherein, in the outputting, in the situation in which there is the difference, output is made in a manner different from the situation in which there is no difference by changing a manner of display of a window.

6. The storage medium storing the program according to claim 1, wherein, in the outputting, output is made in a manner different from the situation in which there is no difference by displaying with highlight a portion in which there is the difference between the first analysis result and the second analysis result.

7. The storage medium storing the program according to claim 6, wherein the display with emphasis is to change or add at least one of a color, shape, letter, and/or mark in the portion in which there is the difference between the first analysis result and the second analysis result and to display the result.

8. The storage medium storing the program according to claim 1, wherein, in the outputting, output is made in a manner different from the situation in which there is no difference by displaying only a portion in which there is the difference between the first analysis result and the second analysis result.

9. The storage medium storing the program according to claim 1, wherein the first medical image is an image imaged at a different date and time from the second medical image.

10. The storage medium storing the program according to claim 1, wherein the computer process includes a process to detect a lesion candidate in the first medical image or the second medical image, and wherein the difference between the first analysis result and the second analysis result includes, a situation in which the lesion candidate detected in the first medical image is not detected in the second medical image or the lesion candidate not detected in the first medical image is detected in the second medical image.

11. The storage medium storing the program according to claim 1, wherein the computer process includes a process to detect a lesion candidate in the first medical image or the second medical image, and wherein the difference between the first analysis result and the second analysis result includes, a size or a range is different in a predetermined amount or more between the lesion candidate detected in the first medical image and the lesion candidate detected in the second medical image.

12. An information processing apparatus comprising a hardware processor configured to execute, acquiring a first analysis result obtained by a computer process on a first medical image of a patient;

acquiring a second analysis result obtained by a computer process on a second medical image of the patient; and comparing the first analysis result and the second analysis result and in a situation in which there is the difference, outputting in a manner different from the situation in which there is no difference, wherein lesion candidates in the first analysis result and the second analysis result are specified with lesion regions, each of the lesion regions having a predetermined shape and size surrounding a center of a respective lesion candidate of the lesion candidates, and the comparing including determining a degree of overlap by calculating a percentage that the lesion regions of the first analysis result and the second analysis result overlap.

13. An information processing method comprising:

acquiring a first analysis result obtained by a computer process on a first medical image of a patient;

acquiring a second analysis result obtained by a computer process on a second medical image of the patient; and comparing the first analysis result and the second analysis result and in a situation in which there is the difference, outputting in a manner different from the situation in which there is no difference, wherein lesion candidates in the first analysis result and the second analysis result are specified with lesion regions, each of the lesion regions having a predetermined shape and size surrounding a center of a respective lesion candidate of the lesion candidates, and the comparing including determining a degree of overlap by calculating a percentage that the lesion regions of the first analysis result and the second analysis result overlap.

14. An information processing system comprising a hardware processor configured to execute, performing a computer process on a first medical image of a patient and generating a first analysis result;

performing a computer process on a second medical image of a patient and generating a second analysis result;

acquiring the first analysis result;

acquiring the second analysis result; and comparing the first analysis result and the second analysis result and in a situation in which there is the difference, outputting in a manner different from the situation in which there is no difference, wherein lesion candidates in the first analysis result and the second analysis result are specified with lesion regions, each of the lesion regions having a predetermined shape and size surrounding a center of a respective lesion candidate of the lesion candidates, and the comparing including determining a degree of overlap by calculating a percentage that the lesion regions of the first analysis result and the second analysis result overlap.

15. The storage medium storing the program according to claim 1, wherein the predetermined shape and size of the each of the lesion regions of the first analysis result and the second analysis result is changeable for each medical facility, department, body part to be imaged, or combinations thereof.

16. The storage medium storing the program according to claim 1, wherein each of the lesion regions of the first analysis result and the second analysis result is a circle with a predetermined radius from the center position of the respective lesion candidate.

* * * * *